United States Patent
Bölt et al.

(10) Patent No.: US 7,566,679 B2
(45) Date of Patent: Jul. 28, 2009

(54) COCATALYST FOR THE PRODUCTION OF LINEAR ALPHA-OLEFINS

(75) Inventors: Heinz Bölt, Wolfratshausen (DE); Peter Fritz, Unterhaching (DE); Holger Hackner, München (DE); Atieh Abu-Raqabah, Riyadh (SA); Mohammed Zahoor, Riyadh (SA); Fuad Mosa, Riyadh (SA)

(73) Assignees: Saudi Basic Industries Corporation, Riyadh (SA); Linde AG, Wiesbaden (DE)

( * ) Notice: Subject to any disclaimer, the term of this patent is extended or adjusted under 35 U.S.C. 154(b) by 0 days.

(21) Appl. No.: 11/660,557

(22) PCT Filed: Jul. 7, 2005

(86) PCT No.: PCT/EP2005/007321

§ 371 (c)(1),
(2), (4) Date: Sep. 24, 2007

(87) PCT Pub. No.: WO2006/018071

PCT Pub. Date: Feb. 23, 2006

(65) Prior Publication Data

US 2008/0176738 A1 Jul. 24, 2008

(30) Foreign Application Priority Data

Aug. 20, 2004 (DE) .................. 10 2004 040 497

(51) Int. Cl.
*B01J 31/04* (2006.01)
*B01J 37/00* (2006.01)
(52) U.S. Cl. .................. 502/170; 502/103; 502/117
(58) Field of Classification Search ............... 502/103, 502/117, 170; 585/523, 522
See application file for complete search history.

(56) References Cited

U.S. PATENT DOCUMENTS

| 3,862,257 A | * | 1/1975 | Buben et al. | ............... 585/523 |
| 4,434,312 A | * | 2/1984 | Langer, Jr. | ............... 585/523 |
| 4,966,874 A | | 10/1990 | Young et al. | |
| 5,449,850 A | | 9/1995 | Young et al. | |
| 2002/0147375 A1 | * | 10/2002 | Tembe et al. | ............... 585/523 |

FOREIGN PATENT DOCUMENTS

| DE | 19812066 | 1/1999 |
| FR | 2689500 | 10/1993 |
| IT | 24498 | 7/1979 |

* cited by examiner

*Primary Examiner*—Ling-Siu Choi
(74) *Attorney, Agent, or Firm*—Kramer Levin Naftalis & Frankel LLP

(57) ABSTRACT

The invention relates to a homogeneous catalyst for the production of linear alpha-olefins by oligomerisation of ethylene, consisting of a zirconium salt of organic acids and a cocatalyst which consists of alkylaluminiums and/or aluminium chloride. The activity of the catalyst, system may sometimes be raised substantially by adjusting the molar ratio of chlorine to aluminium in the cocatalyst within the range between 1.0 and 1.5. The economic viability of the production process and product purity are improved.

1 Claim, 1 Drawing Sheet

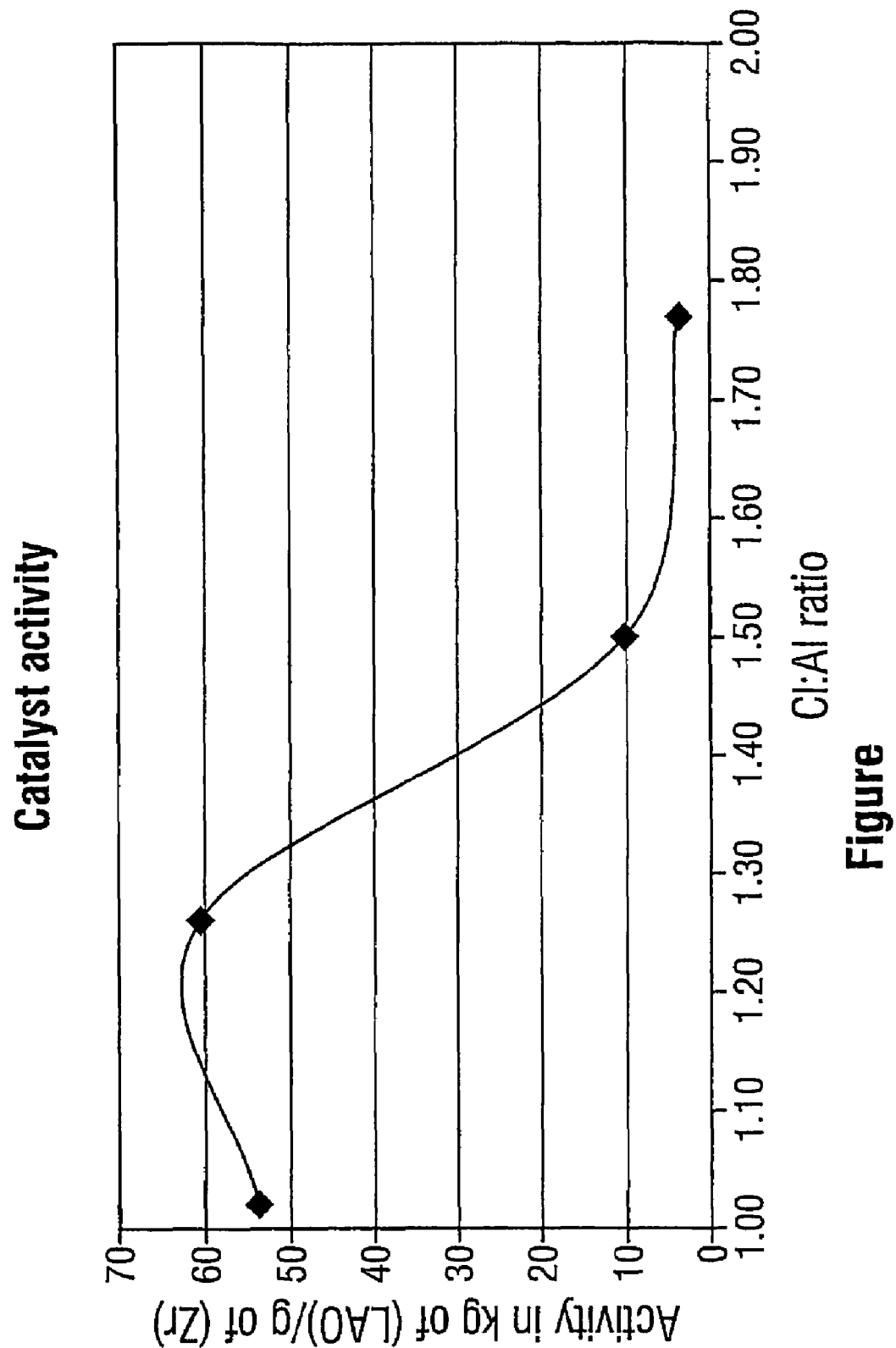

COCATALYST FOR THE PRODUCTION OF LINEAR ALPHA-OLEFINS

The invention relates to a homogeneous catalyst for the production of linear alpha-olefins by oligomerisation of ethylene, consisting of a zirconium salt of organic acids and a cocatalyst.

Linear alpha-olefins (LAO), for example those with four to 30 carbon atoms, are compounds which are, for example, widely used and required in large quantities as comonomers for modifying the properties of polyolefins or as a starting material for the production of plasticisers, household cleansers, flotation agents, emulsifiers, drilling fluids, surface-active substances and synthetic oils, putties, sealants and the like.

According to the inventions described in USSR inventor's certificate 1042701A, the unaccepted Italian patent application ITA24498A/79 and German patents DE4338414 and DE4338416, the oligomerisation of ethylene to C4-C30 LAO is performed in an organic solvent at 60 to 80° C. and pressures of 2.0 to 4.0 MPa. Toluene, benzene or heptane are used as reaction media. All these processes make use of catalysts which consist of a zirconium salt of an organic acid and one of the alkylaluminiums $Al(C_2H_5)_3$, $Al_2Cl_3(C_2H_5)_3$ or $AlCl(C_2H_5)_2$ as cocatalyst. In order to prevent the occurrence of unwanted secondary reactions, it is necessary to terminate the oligomerisation immediately the reaction mixture leaves the reactor. The catalyst is deactivated by addition of a polar oxygen compound ($H_2O$, methanol, ethanol, carboxylic acids etc.) to the reaction mixture and is then separated from the mixture by adsorption onto a regeneratable aluminium oxide gel. The deactivated catalyst must be replaced by fresh material.

The high price of the zirconium salt means that the catalyst accounts for a considerable proportion of the operating costs of the processes. Higher activity of the catalyst (expressed in kg of LAO product/g of Zr) results in lower consumption and thus in increased economic viability of LAO production because operating costs and, due to the consequently possible reduction in size of the apparatuses for storing, apportioning, deactivating and removing the catalyst, also capital costs are reduced.

It is accordingly an object of the present invention to increase the activity of the catalyst hitherto used for LAO production by modifying the chemical composition thereof in such a manner that lower catalyst consumption is achieved without any drop in product quality.

This object is achieved according to the invention in that the cocatalyst is produced as a mixture of alkylaluminiums and/or aluminium chloride, wherein the molar ratio of chlorine to aluminium in the cocatalyst may be adjusted at will within a certain range by modifying the proportions of the various compounds in the mixture.

DE4338414 describes a catalyst system which is conveniently used in connection with the process explained therein. The zirconium compound has the chemical formula $ZrCl_mX_n$, wherein $m+n=4$, $0 \leq m \leq 2$ and X denotes a carboxylate derived from a $C_4$ to $C_9$ fatty acid. The compound $Al_2Cl_3(C_2H_5)_3$ has proved to be a particularly advantageous cocatalyst in practice, giving rise to a catalyst activity of 10 kg of (LAO) per 1 g of (Zr).

It has been found that the decisive parameter determining the level of catalyst activity is the molar ratio of chlorine to aluminium in the cocatalyst. Given suitable selection of this ratio, values considerably higher than 10 kg of (LAO)/g of (Zr) may be achieved. Product purity is simultaneously improved.

The cocatalyst is preferably mixed from the substances $Al(C_2H_5)_3$ and/or $AlCl(C_2H_5)_2$ and/or $Al_2Cl_3(C_2H_5)_3$ and/or $AlCl_2(C_2H_5)$ and/or ($AlCl_3$) such that a Cl:Al ratio with a value of between 1.0 and 1.5 is obtained. The Cl:Al ratio particularly preferably has a value of between 1.0 and 1.3.

BRIEF DESCRIPTION OF THE DRAWING

In the FIGURE, catalyst activity is plotted as a function of the molar ratio of Cl to Al in the cocatalyst. Starting from an activity of 10 kg of (LAO)/g of(Zr) at a Cl:Al ratio of 1.5, corresponding to the prior art ($Al_2Cl_3(C_2H_5)_3$), activity rapidly rises as the value of the ratio drops until, at Cl:Al=1.26, it is approximately 500% above the prior art. Activity then slowly drops back down to reach a value of approximately 54 kg of (LAO)/g of (Zr) at Cl:Al=1.02. If Cl:Al ratios of higher than 1.5 are used, activity drops. At Cl:Al=1.77, it is only 3.1 kg of (LAO)/g of (Zr).

The invention claimed is:

1. A homogeneous catalyst for the production of linear alpha-olefins by oligomerization of ethylene, comprising a zirconium salt having the chemical formula $ZrCl_mX_n$, wherein $m+n=4$, $1 \leq m \leq 2$ and X is a carboxylate a $C_4$ to $C_9$ organic acid and a cocatalyst which consists essentially of two or more compounds selected from the group consisting of $Al(C_2H_5)_3$, $AlCl_3$, $AlCl(C_2H_5)_2$, $AlCl_2(C_2H_5)$ and $Al_2Cl_3(C_2H_5)_3$, wherein the molar ratio of chlorine to aluminum in the cocatalyst is within the range of 1.0 to 1.3.

* * * * *